United States Patent
Ngo et al.

(10) Patent No.: US 7,781,573 B2
(45) Date of Patent: Aug. 24, 2010

(54) MULTI LAYER CHROMATOGRAPHY OF NUCLEIC ACIDS

(76) Inventors: Nam Q Ngo, 4191 Rincon Ave., Campbell, CA (US) 95008; Laurent Jaquinod, 3143 Woods Cir., Davis, CA (US) 95616

( * ) Notice: Subject to any disclaimer, the term of this patent is extended or adjusted under 35 U.S.C. 154(b) by 404 days.

(21) Appl. No.: 11/888,490

(22) Filed: Jul. 31, 2007

(65) Prior Publication Data
US 2008/0033158 A1  Feb. 7, 2008

Related U.S. Application Data

(60) Provisional application No. 60/835,131, filed on Aug. 3, 2006.

(51) Int. Cl.
  C07H 21/02 (2006.01)
  C07H 21/04 (2006.01)
  C07H 1/06 (2006.01)
(52) U.S. Cl. ............... 536/23.1; 536/24.33; 536/25.4; 536/25.41; 536/127
(58) Field of Classification Search .................. None
  See application file for complete search history.

(56) References Cited

U.S. PATENT DOCUMENTS 6,649,751 B2 * 11/2003 Usman et al. ............... 536/25.4
7,425,700 B2 * 9/2008 Stults et al. .................. 250/288

OTHER PUBLICATIONS

Lyttle et al., "New Nucleoside Phosphoramidites and Coulping protocols for Solid-Phase RNA synthesis" Journal of Organic Chemistry (1991) vol. 56 pp. 4608-4615.*
"Vydac HPLC Columns" technical bulletin published online at www.chromtech.com/Catalog7/PDF_Indvpge/122.pdf.*
"The Concept of a Resolution Mixture in Developing and Validating Process Chromatographic Methods, Application Note 9809" Published online www.nestgrp.com/pdf/Vapp/AN9809.pdf, pp. 1-2.*
Brown et al., "Synthesis of a benzotriazole phosphoramidite for attachment of oligonucleotides to metal surfaces" Tetrahedron Letters (2001) vol. 42 pp. 2197-2200.*

Gilar et al., "Purification of crude DNA oligonucleotides by solid-phase extraction and reversed-phase high-performance liquid chromatography" Journal of Chromatography A (2000) vol. 890 pp. 167-177.*
Dellinger et al., "Solid-Phase Chemical Synthesis of Phosphonoacetate and Thiophosphonoacetate Oligodeoxynucleotides" Journal of the American Chemical Society (2003) vol. 125 pp. 940-950.*
"Vydac HPLC Columns" technical bulletin published online at www.chromtech.com/Catalog7/PDF_Indvpge/122.pdf downloaded Oct. 17, 2009.*
"The Concept of a Resolution Mixture in Developing and Validating Process Chromatographic Methods, Application Note 9809" Published online www.nestgrp.com/pdf/Vapp/AN9809.pdf, pp. 1-2, downloaded Oct. 17, 2009.*
Lyttle et al., "New Nucleoside Phosphoramidites and Coupling Protocols for Solid-Phase RNA Synthesis" Journal of Organic Chemistry (1991) vol. 56, pp. 4608-4615.
"The Concept of a Resolution Mixture in Developing and Validating Process Chromatographic Methods, Application Note 9809" Published online www.nestgrp.com/pdf/Vapp/AN9809.pdf, pp. 1-2, Downloaded Oct. 17, 2009.
Brown et al., "Synthesis of a benzotriazole phosphoramidite for attachment of oligonucleotides to metal surfaces" Tetrahedron Letters (2001) vol. 42, pp. 2197-2200.

* cited by examiner

*Primary Examiner*—Eric S Olson
(74) *Attorney, Agent, or Firm*—Schneck & Schneck

(57) ABSTRACT

Methods using two to (n) purification columns to separate full length 5'-DMT-on oligonucleotides with size ranging from 40 to 180-mers from short length 5'-DMT-on oligonucleotides. Two of the said methods require using some columns sequentially with the collection and reprocessing of an intermediate fraction and are used for oligonucleotides with length ranging from 70 to 180-mers. A third method is carried out with columns stacked and used in series and is best used to purify oligonucleotides with length ranging from 40 to 80-mers. In the presence of a high ionic strength buffer, the short length DMT-on oligonucleotides bind to the top stacked columns while the less hydrophobic contaminant or DMT-off failures do not bind and/or are being washed off. In a stacked configuration, the full length DMT-on oligonucleotides are retained by the bottom column while in a 15 sequential configuration, full length DMT-on oligonucleotides are collected and reprocessed.

33 Claims, 11 Drawing Sheets

MULTI LAYER CHROMATOGRAPHY OF NUCLEIC ACIDS

PRIORITY

This application claims benefit of provisional application 60/835,131, filed Aug. 3, 2006.

BACKGROUND OF THE INVENTION

Nucleic acids are synthesized using solid supports and 5'-dimethoxytrityl protected phosphoramidite reagents (Beaucage, 1981; Caruthers, 1983). After completion of a synthesis, they are cleaved from the synthesis supports either as their 5'-unprotected form (DMT-off oligonucleotides) or as their 5'-dimethoxytrityl protected form (DMT-on oligonucleotides).

DMT-off oligonucleotides, notably long oligonucleotides, are desalted or purified by way of high-performance liquid chromatography (Ikuta, 1984) or polyacrylamide gel electrophoresis. DMT-on oligonucleotides are best purified by Solid-Phase Extraction (SPE) using disposable cartridges prepacked with reversed-phase sorbents such as silane-modified controlled pore glass (CPG) or cross-linked polystyrenes (Andrus, 1993; Semenyuk, 2006). The said sorbents reversibly adsorb DMT-on oligonucleotides by taking advantage of the hydrophobic handles provided by the 5'-dimethoxytrityl groups (Cashion, 1973) while polar DMT-off failures, salts and organic impurities are effectively eliminated in the flow-through and subsequent washing steps. Subsequent on-cartridge detritylation of DMT-on oligonucleotides and elution yield the corresponding purified DMT-off oligonucleotides.

SPE purification is the method of choice for full length DMT-on oligonucleotides with fragment less than 40 bases. Its shortcoming stems from the plurality of DMT-on species generated during synthesis and deprotection. Full length oligonucleotides are invariably contaminated with short length DMT-on oligonucleotides arising from depurination (Horn, 1988) or branching (Pon, 1985). Increased contaminations in long oligonucleotides hinder the use of SPE columns. Commercial suppliers recommend long oligonucleotides to be purified by HPLC or PAGE, therefore preventing their widespread use due to high processing costs.

Methods and reagents capable of isolating long oligonucleotides from short length DMT-on oligonucleotides, in a manner that avoids limitations to the current systems, are urgently needed. The present invention describes a multimodal cartridge system or Multi Layer Chromatography (MLC) that efficiently separates full length DMT-on nucleic acids from hydrophobic contaminants. The said MLC system is readily amenable to a high throughput purification of long oligonucleotides up to 200-mers and could substantially contributes to the field of molecular biology (gene synthesis, hybridization probes, long primers etc) by making pure long oligonucleotides quickly available at a fraction of the current costs.

BRIEF SUMMARY OF THE INVENTION

Oligonucleotides are synthesized on automated workstations using solid-phase methodologies and phosphoramidite chemistry. Following trityl-on synthesis, cleavage from the solid support and deprotection, a crude product is obtained containing the desired full-length DMT-on oligonucleotides together with DMT-on and DMT-off truncated sequences. Most disposable SPE cartridges prepacked with reversed-phase sorbents such as OPC®, Top, Mop, Clarity or Sep-Pak™ (commercialized by Applied Biosystems, Varian, CTGen, Phenomenex or Waters, respectively) efficiently separate DMT-on oligonucleotides (less than 50-mers) from DMT-off failures. Technological challenges lay in the separation of full length (FL) DMT-on oligonucleotide from short length (SL) DMT-on oligonucleotide as they are both retained by hydrophobic interactions with the sorbent non polar surfaces.

HPLC analyses of long DMT-on oligonucleotides (40 to 150-mers) and capping dummy experiments (vide infra) evidenced that the proportion of SL DMT-on oligonucleotides increase dramatically with the increasing size of the oligonucleotide synthesized. SL DMT-on oligonucleotides arise from branching occurring during synthesis using DMT-on protected phosphoramidite reagents or from depurination. Apurinic sites, generated by the repetitive exposure of DMT-on oligonucleotides to acidic reagents used during the detritylation steps of a nucleic acid synthesis, are cleaved by bases during the cleaving and deprotection steps yielding 5'-DMT-on truncated oligonucleotides (Horn et al). Increased presence of branched DMT-on oligonucleotides was evidenced by carrying out dummy couplings at position 21 during the synthesis of a series of DMT-on 75-mers oligonucleotides. Acetonitrile was delivered instead of an amidite and resulting in the absence of coupling at the said position 21. All 20-mers or other oligonucleotide fragments of any length bound to the synthesis supports were capped during the subsequent capping step, thus preventing any further extension to occur. Therefore, no DMT-on oligonucleotides should be detected by HPLC upon completion of the 75-mer synthesis cycles. Indeed, no full length DMT-on oligonucleotide was found. However, numerous SL DMT-on oligonucleotides were observed (see FIG. 1). Such branching was little present when the synthesis of a 75-mer poly-T was dummied at position 21 but increased considerably with increasing G content in the 75-mers sequences. This confirmed that separation of long oligonucleotides solely on the basis of the hydrophobic character provided by a 5'-hydrophobic end was not sufficient and that additional selectivity was required to purify FL oligonucleotides.

We developed a multimodal SPE system relying on a plurality of retainment layers, wherein each reversed-phase layer excludes or hydrophobically binds DMT-on oligonucleotides accordingly to their sizes, while DMT-off oligonucleotides are eluted unretained. Multimodal SPE refers to the intentional use of more than one retention mechanism in order to effectively clean-up interfering substances (R. E. Majors, 2007).

A MLC system is made of plurality of columns which can be stacked and used in a series or can be used sequentially. The columns are prepacked with reversed-phase sorbents such as C8, C18, Phenyl-CPG, or tritylmercaptopropyl-CPG. Full length DMT-on oligonucleotides are separated from DMT-on failures by taking advantage in their differences in sizes. Quantity of reversed-phase sorbent and pore size are optimized such as SL DMT-on oligonucleotides bind to the top cartridges and full length DMT-on oligonucleotides bind to the bottom cartridge while other components are washed through. Short length DMT-on oligonucleotides diffuse faster than long DMT-on oligonucleotides through a matrix containing pores with well-defined diameters. In the presence of a binding buffer with high ionic strength, this differential diffusion leads to the preferential binding of short length DMT-on oligonucleotides to the sorbent hydrophobic surfaces.

Three preferred methods were designed to isolate full-length DMT-on oligonucleotides with length about 40 to 180- mers using (n) stacked columns C, wherein (n) is at least equal to two. A first method is carried out with stacked columns in a series and is best used to purify oligonucleotides with length ranging from 40 to 80-mers. Two methods of the invention require using some columns sequentially with the collection and reprocessing of an intermediate fraction. Those methods are used for oligonucleotides with length ranging from 70 to 180-mers.

As an example, there are six main steps in the multimodal SPE purification of FL oligonucleotides with length ranging from 40 to 80-mers: (a) Diluting the crude DMT-on nucleic acid solution with a binding buffer; (b) Loading the resulting solution; (c) Discarding flow-through and top C(1) to C(n−1) columns; (d) Washing the bottom C(n) column; (e) Detritylating DMT-on nucleic acids adsorbed on said C(n) column and (f) Eluting purified DMT-off oligonucleotide. By skipping step (e), FL DMT-on oligonucleotides are eluted. Typically, full length oligonucleotides are obtained with purity ranging from 90 to 95%.

The term nucleic acid or oligonucleotide as used herein is defined as a molecule comprised of two or more deoxyribonucleotides or ribonucleotides, preferably more than three, and usually more than ten. The term "long oligonucleotide" as used herein is defined as a molecule comprised of 40 or more deoxyribonucleotides or ribonucleotides. The term oligonucleotide also refers to ribonucleic acid or deoxyribonucleic acid, in which modifications can take place at the level of the base (such as inosine, methyl-5-deoxycytidine, and deoxyuridine), the ribose rings or the internucleotide phosphate bonds in a chemically known manner. Depending on whether the nucleic acid is DNA or RNA, the nitrogen base is selected from adenine, guanine, cytosine, thymine or uracil. The term "crude" describes synthetic mixtures containing full length DMT-on oligonucleotide (FL DMT-on) and at least two contaminants wherein one of the said contaminant is a short length DMT-on oligonucleotide (SL DMT-on) and another is a DMT-off oligonucleotide. Oligonucleotides can be prepared by any suitable chemical synthesis such as the phosphotriester method, the phosphodiester method or the phosphoramidite method.

BRIEF DESCRIPTION OF THE SEVERAL VIEWS OF THE DRAWING

FIG. 3A: Chromatographic analysis of a crude DMT-on 70-mers.

FIG. 3B: Chromatographic analysis of the flow-through collected after loading the said crude DMT-on 70-mers.

FIG. 3C: Chromatographic analysis of SL DMT-on oligonucleotides.

FIG. 3D: Chromatographic analysis of purified full length DMT-on 70-mers.

FIG. 4A: Chromatographic analysis of a crude DMT-on 125-mers.

FIG. 4B: Chromatographic analysis of the first flow-through collected after loading the said crude DMT-on 125-mers.

FIG. 4C: Chromatographic analysis of SL DMT-on oligonucleotides.

FIG. 4D: Chromatographic analysis of the second flow-through.

FIG. 4E: Chromatographic analysis of purified full length DMT-on 125-mers.

DETAILED DESCRIPTION OF THE INVENTION

Figure 1:
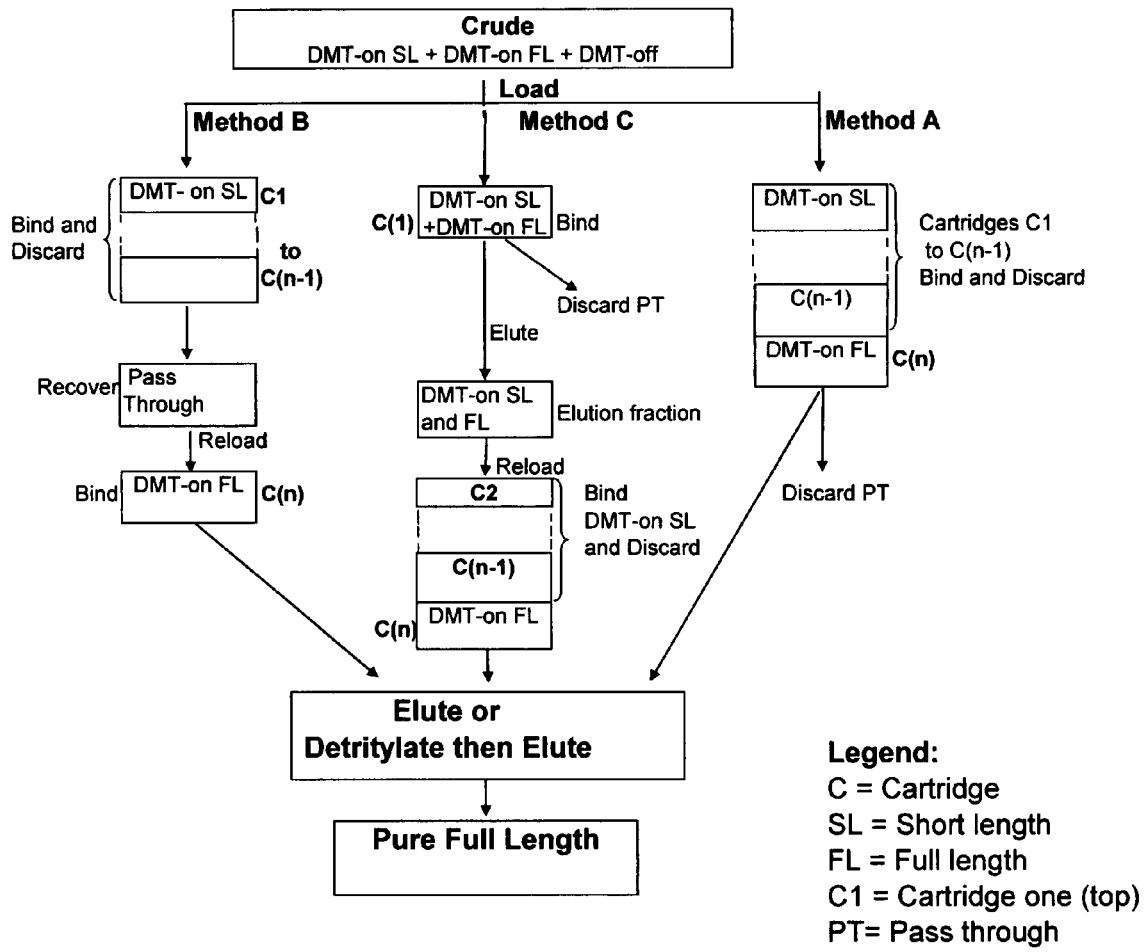
FIG. 1: Chromatographic analysis showing branched DMT-on oligonucleotides.

The present invention relates to the multimodal Solid-Phase Extraction (SPE) of full length oligonucleotides from synthetic crudes. Particularly, methods for separating and isolating long oligonucleotides which sizes ranging from about 40 to 180-mers are disclosed. SPE is a powerful purification technique for clean-up of DMT-on oligonucleotides less than 50-mers in length. Compared to HPLC and PAGE purifications, current trityl-on methods using SPE provide major advantages in terms of rapidity, simplicity, high throughput, and lower costs. A major drawback is that short length (SL) DMT-on oligonucleotides are isolated along with the full length (FL) DMT-on oligonucleotides making the said trityl-on methods inappropriate in purifying long FL oligonucleotides as the proportion of isolated SL DMT-on oligonucleotides increases dramatically with the length of the synthesis.

To isolate full-length oligonucleotides from a crude solution containing short length DMT-on oligonucleotides and failures DMT-off oligonucleotides, the present invention relies on using a plurality of SPE columns. The terms column, syringe, cartridge, or pipette tip can be used interchangeably. All SPE devices used in the present invention are stackable, to be used with an adapter if needed, and are processed using standard SPE vacuum manifolds. Typically, there are four standard operations in SPE processing: preequilibrating the columns, loading sample, washing and elution. Solutions used during those operations are drawn through the stacked columns by vacuum. Columns can be vacuum-dried during the purification process in order to further eliminate contaminants.

Sorbents used in the present invention are made of porous materials selected from silica or controlled porous glass (CPG). Reversed-phase CPG is available from numerous commercial sources or prepared by silane modification of controlled porous glass, wherein the said silanes introduce non polar groups onto the sorbent surface. Preferably, endcapped alkyl-CPG or endcapped aryl-CPG are used, wherein endcapping with trialkylsilanes is carried out to cap unreacted silanol groups at the sorbent surfaces. Preferentially, commercially available endcapped C8-CPG, C18-CPG, Phenyl-CPG or tritylmercaptopropyl-CPG (from Chemistry and Technology for Genes, Milpitas, Calif.) are used. Said sorbents can be embedded with polymers particles, for example high molecular weight polyethylene beads, and sintered into plug like materials. All SPE devices are packed with a predetermined amount of reversed-phase sorbent or with plugs containing a predetermined amount of reversed-phase sorbent. Preferably, stackable pipette tips which are packed with tritylmercaptoalkyl-CPG beads embedded in polyethylene are used.

Stacked SPE columns contain porous reversed-phase sorbents which may be identical but preferentially differ in pore size. Columns are defined by their approximate loading capacity and the pore size of the porous sorbent used. Preferably, the said sorbents are made of spherical particles with diameter in the range of 10-180 microns and preferentially 20-45 microns. Porous means that the sorbents contain pores having substantially similar size in the range between 20 ∪ to 1000 Å. Preferably, the pore sizes are about 30 Å to 300 Å. Exclusion or cutoff limits of the top columns containing porous material are determined by the particle diameter and their pore size. For example, SL DMT-on oligonucleotides from a 50-mers, 80-mers or 120-mers syntheses are best retained by using resins with pore size about 60 Å, 60-100 Å and 100-150 Å, respectively.

Figure 2:
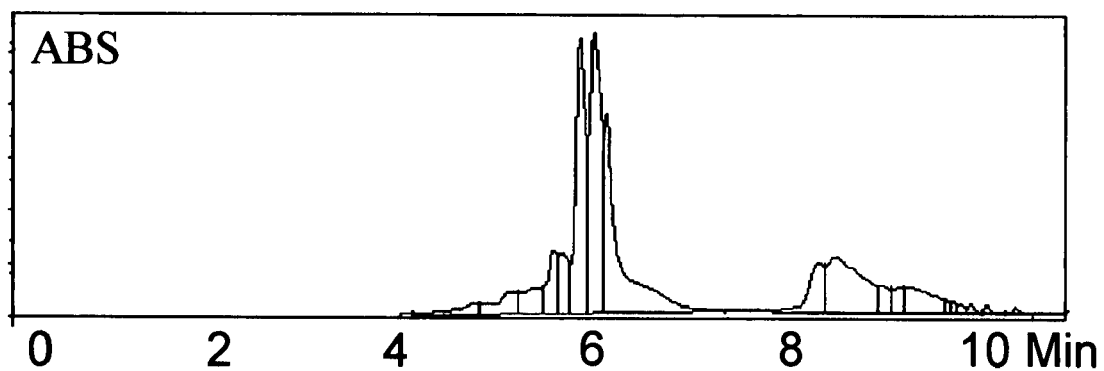
FIG. 2: Diagram of protocols to separate FL DMT-on oligonucleotides from SL DMT-on and DMT-off oligonucleotides.

Three multimodal SPE methods (A, B and C) of the invention, summarized in FIG. 2, rely on using two to (n) purification columns. They involve binding and discarding SL DMT-on oligonucleotides prior to isolate FL DMT-on oligonucleotides but differ in their processing set-ups. Methods B and C require using some columns sequentially with the collection and reprocessing of an intermediate fraction while method A is carried out with columns stacked and used in series. Choosing an appropriate method depends on the size and quality of the syntheses. Preferably, method A is used for oligonucleotides with length ranging from 40- to 80-mers while sequential methods B or C are used for oligonucleotides with length ranging from 70- to 180-mers and require additional processing steps. 180-mers was the upper limit tested but we are confident that oligonucleotides 200-mers and plus can be purified using the same protocols.

The SPE columns, prepacked with hydrophobic resins, are first equilibrated with 40% acetonitrile in water then with a water buffer containing lower primary, secondary or tertiary alkylammonium and mixtures of one or more thereof. Preferably, acetate salts of triethylammonium or diisopropylethylammonium or t-butylammonium are used. Each column can be primed separately using different buffers in order to optimize specific binding. Prior loading, the crude oligonucleotide solution typically in aqueous ammonia or methylamine/ammonia solutions are diluted with a high salt binding buffer in a 2:1 to 1:3 volume/volume. The presence of salt promotes hydrophobic interactions with the sorbent hydrophobic surface. Preferably, a binding buffer contains 10 to 35% sodium chloride in water. Preferentially, 15 to 30% sodium chloride in water is used. Other salt can be used such as ammonium sulfate, ammonium chloride, ammonium bromide, sodium bromide, sodium iodide, potassium chloride, potassium bromide, potassium iodide. Failures to add a binding buffer results in low binding and low recovery.

In a first embodiment, method A is set up by stacking two or more columns in a series allowing for the simultaneous extraction and separation of FL DMT-on oligonucleotides from SL DMT-on oligonucleotides while DMT-off oligonucleotides are unretained. Method A is best performed by ensuring that all DMT-on products are retained by the sorbents with none to be found in the flow-through. The top columns in a series contain reversed-phase sorbents with smaller pores that bind preferentially SL DMT-on oligonucleotides by a restricting diffusion of FL DMT-on oligonucleotides within the pores. Competitive adsorption of SL DMT-on oligonucleotides is further enhanced by using high salt binding buffer. Full length DMT-on oligonucleotides bind preferentially to the bottom cartridges packed with reversed-phase sorbents having wider pore size while the DMT-off failures do not bind and are being washed off. Method A includes the following steps:

(a) Stacking of two or more columns containing reversed-phase sorbents. Preferentially, columns prepacked with tritylmercaptopropyl-CPG (MOP resin from CTGen, Milpitas, Calif.) are being used wherein the top C(1) to C(n-1) columns contain beads with pore size ranging from 40 Å to 150 Å and wherein the bottom C(n) column contains beads with pore size ranging from 100 Å to 300 Å. Preferentially, the C(1) to C(n-1) contain beads with pore size ranging from 60 Å to 100 Å and the bottom C(n) column contains beads with pore size ranging from 200 Å to 300 Å.

(b) Equilibrating stacked columns first with a solution of 40% acetonitrile in water then with a TEAA buffer (triethylammonium acetate, 0.1 M to 1 M, pH 6 to 7.5).

(c) Diluting the crude solution with a high salt binding buffer and loading the resulting mixture onto the top column. Flow-through, containing unretained DMT-off oligonucleotides, is discarded.

(d) Discarding C(1) to C(n-1) columns containing bound short length DMT-on oligonucleotides.

(e) Washing non-tritylated failures off the bottom C(n) column using a 0.1 M TEAA buffer (pH 7, 2 mL) or a low salt buffer containing a small percentage of an organic modifier. Preferably, a low salt buffer containing 2 to 8% of dimethylformamide (DMF), DMSO, methanol, ethanol, t-butylamine or acetonitrile is used. Preferentially, a washing buffer containing a small percentage of sodium chloride and DMF in water is used.

(f) Treating bound FL DMT-on oligonucleotides with a 5'-DMT-deblocking buffer such as 3% dichloroacetic acid in water resulting in their conversion to the corresponding deprotected form. Purified full length DMT-on oligonucleotides can be recovered by skipping step (f).

(g) Reequibrating the column by washing with 0.1 M TEAA buffer (pH 7, 2 mL).

(h) Eluting and collecting full length oligonucleotides wherein the eluting buffer comprises 20 to 60% by volume of an alcohol selected from the group consisting of methanol, ethanol and isopropanol or 25 to 65% by volume of nitrile such as acetonitrile or a 10-25% ammonia solution or 10 to 30% t-butylamine or combinations thereof. Preferentially, 40% ethanol or 40 to 60% acetonitrile are used.

Typically, a synthesis of 60-80-mers on a 100 nmol scale yields around 40 ODs of crude and contains around 55% of FL DMT-on oligonucleotides and 15% of SL DMT-on oligonucleotides. The said crude, treated according to method A, yields five to ten ODs of purified oligonucleotides with purity ranging from 85 to 95%. Method A offers the opportunity for scalability and fast turnaround. Oligonucleotides purified by this method have proven to be successful primers for gene synthesis.

In a second embodiment, a sequential method (FIG. 2, Method B) of isolating full length oligonucleotides from a crude deprotection sample diluted with a binding buffer includes three main events: (i) Binding and discarding SL DMT-on oligonucleotides (ii) Recovering the flow-through containing DMT-on full length and DMT-off oligonucleotides (iii) Loading said flow-through and binding FL DMT-on oligonucleotides. Method B is particularly useful for purifying nucleic acids with a fragment length of about 80 bases or more and comprises the following steps:

(a) Stacking up of two or more columns containing porous reversed-phase sorbents on a vacuum manifold tray. Preferably, columns prepacked with tritylmercaptopropyl-CPG (MOP resin from CTGen, Milpitas, Calif.) are being used wherein the CPG beads have pore size ranging from 40 Å to 150 Å. Preferentially, the top column and the second column have beads with pore size of 60 Å and 100 Å, respectively.

(b) Equilibrating the said columns with a solution containing acetonitrile in water, then a second solution containing a 0.1 M to 1 M concentration of monoalkylammonium or dialkylammonium or trialkylammonium acetate at a pH ranging from 6 to 9.5. Preferably, 40% acetonitrile in water then 0.1 M triethylammonium acetate (pH 6.0 to 7.5) are used.

(c) Diluting crude deprotection solution with a high salt binding buffer in a 1:1 to 1:3 volume/volume and loading the resulting solution. The said binding buffer has a salt concentration of sodium halide or potassium halide ranging between 15 to 35%.

(d) Collecting flow-through containing full length DMT-on oligonucleotides and DMT-off oligonucleotides.

(e) Priming a new column as described in step (a), and loading said flow-through collected in step (d). Eventually, the said flow-through ionic strength and organic concentration may be adjusted by adding a second binding buffer containing sodium chloride and an organic modifier such as DMF, DMSO, primary, secondary or tertiary alkyl amines.

(f) Discarding flow-through and washing bound FL DMT-on nucleic acids with a washing buffer which removes slightly-bound contaminants and DMT-off truncated species, wherein the washing buffer has a pH between 7 and 9 and contains a low salt concentration and a few percent of an organic modifier such as DMF, DMSO, primary, secondary or tertiary alkylamines, acetonitrile, methanol, ethanol or isopropanol.

(g) Cleaving dimethoxytrityl groups with a 5'-DMT-deblocking buffer such as 3% dichloroacetic acid in water, followed by washing with a washing buffer containing 0.1 M TEAA (pH 7 to 9).

(h) Eluting the bound nucleic acids from the bottom column, wherein the eluting buffer contains 20 to 60% by volume of an alcohol selected from the group consisting of methanol, ethanol and isopropanol or 25 to 65% by volume of acetonitrile or 15-25% ammonia solution.

A purified full length DMT-on oligonucleotide can be recovered by skipping step (g). Full length DMT-on oligonucleotides can be further reloaded on the same bottom column which has been first reequilibrated in order to further eliminate, if necessary, remaining traces of DMT-off contaminants.

In a third embodiment, a second sequential method (FIG. 2, Method C) of separating full length oligonucleotides from a crude sample diluted with a binding buffer by using a plurality of columns comprises the following steps: (a) priming a first series of two or more stacked stacked columns containing porous reversed-phase sorbents (b) loading and binding full length and short length DMT-on oligonucleotides using binding conditions ensuring that all hydrophobic species bound to the sorbents; (b) eluting DMT-on oligonucleotides from all or just the bottom column, (c) evaporating and dissolving in a binding buffer; (d) loading the resulting solution on a second series of two or more stacked columns; (e) discarding second flow-through and C(1) to C(n−1) columns; (f) washing DMT-off contaminants off the bottom column; (g) detritylating and washing; (h) eluting target compound. Again, a purified DMT-on can be recovered by skipping the detritylation step. Priming, washing detritylating and eluting buffers have compositions identical to those described in method B.

Full length oligonucleotides are eluted from the bottom column with a solution containing a sufficient concentration of organic solvent. Typical purities of full length oligonucleotides range in 85 to 95% purity. Increasing the total loading capacity of top C(1) to C(n−1) columns reduces yield of full length oligonucleotides but increases their purity.

Oligonucleotide length, quality of synthesis, quantity of crude and proportions of DMT-off failures and SL DMT-on oligonucleotides are some parameters to consider optimizing the present invention. The short process times of the vacuum based purification protocols make them ideally suited for purification in a high-throughput setting. The bottom stacked columns can be secured on a base plate (conforming to the standard 96-well plate format) and set up on a vacuum tray manifold. The number of columns to be stacked is function of the loading capacity of the sorbents, the quantity of ODs of crude oligonucleotides and of the purity and yield required by the end-users. Purification of a full 96-plate requires 10 min of user set-up time, plus 30 to 60 min of purification time depending on the multimodal method used, method A being the fastest.

Although the invention has been described in details for the purpose of illustration, it is understood that such details are solely for that purpose and variations can be made therein by those skilled in the art without departing from the spirit and scope of the invention. The following examples illustrate the invention without limiting it:

EXAMPLES

A first example describes the purification of a 70-mers oligonucleotide using two stacked columns according to the method A of this invention. A second example describes the sequential purification of a 125-mers oligonucleotide according to the method B of this invention. Mercaptotritylpropyl-CPG (MOP resin, Chemistry and Technology for Genes, Milpitas, Calif.) is used with a loading capacity of around 50 nmol for 25-30 mg of resin and comprise beads with pore size around 60 Å to 300 Å). In these experiments, selecting the appropriate and suitable number of columns is dictated by parameters such as the pore sizes, priming pH, ionic strength, organic modifiers, quality of synthesis, and quantity of crude and relative percentages of FL and SL DMT-on oligonucleotides. Concentration of oligonucleotides is given in OD by measuring their optical density at 260 nm. Some parameters such as buffer composition and ionic strength are of foremost importance to enhance selective binding of the oligonucleotides based on their size and hydrophobic characters. Column descriptions include the loading capacity and porosity of the sorbent. As an example, C(1)(50/60) stands for the top column packed with beads having an estimated total loading capacity of 50 nmol and 60 Å pore size.

Example 1

Figure 3A:
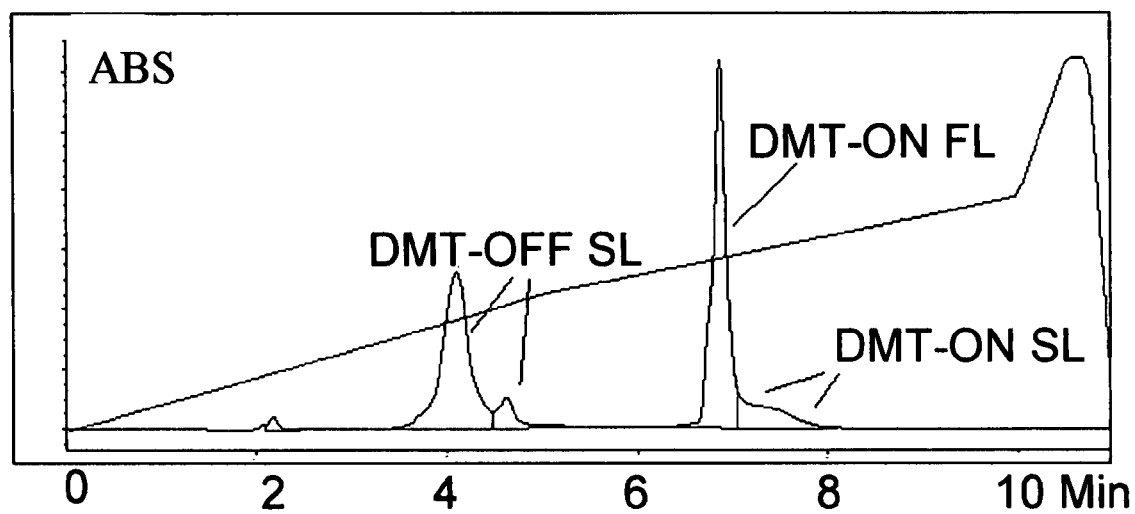
FIGS. 3A to 3D illustrate the purification of a crude DMT-on 70-mers according to method A.
Figure 3B:
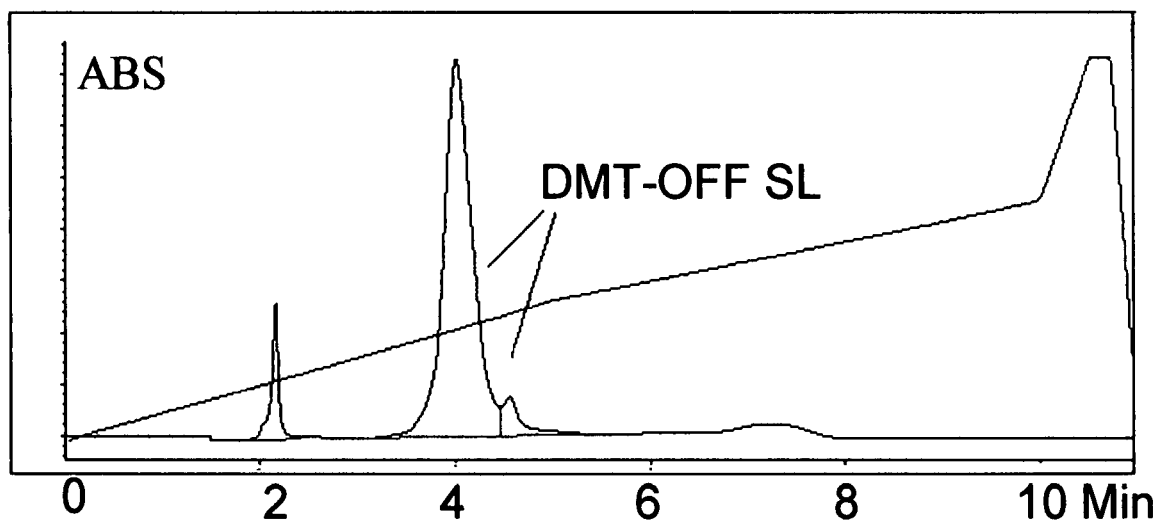
Figure 3C:
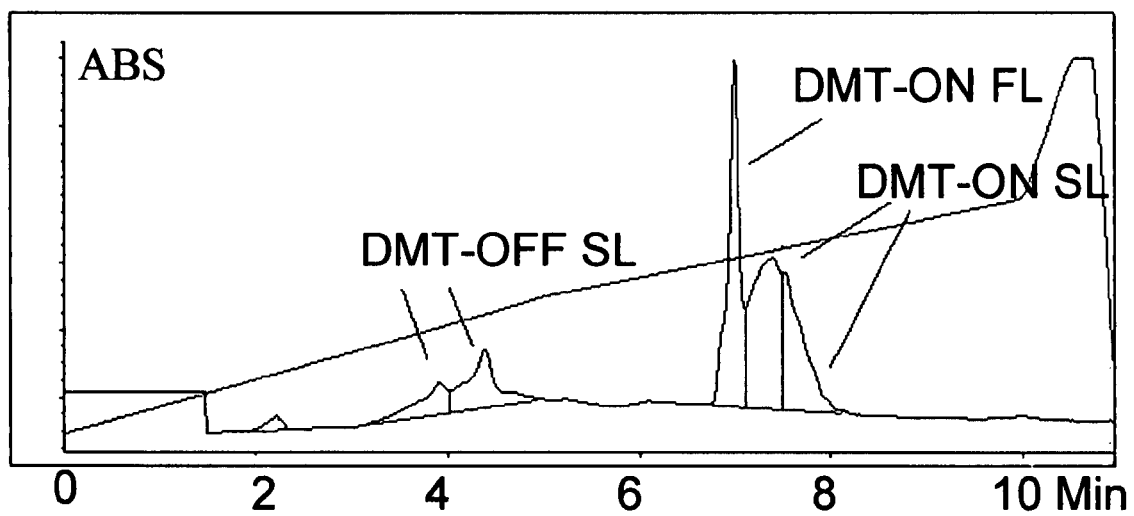
Figure 3D:
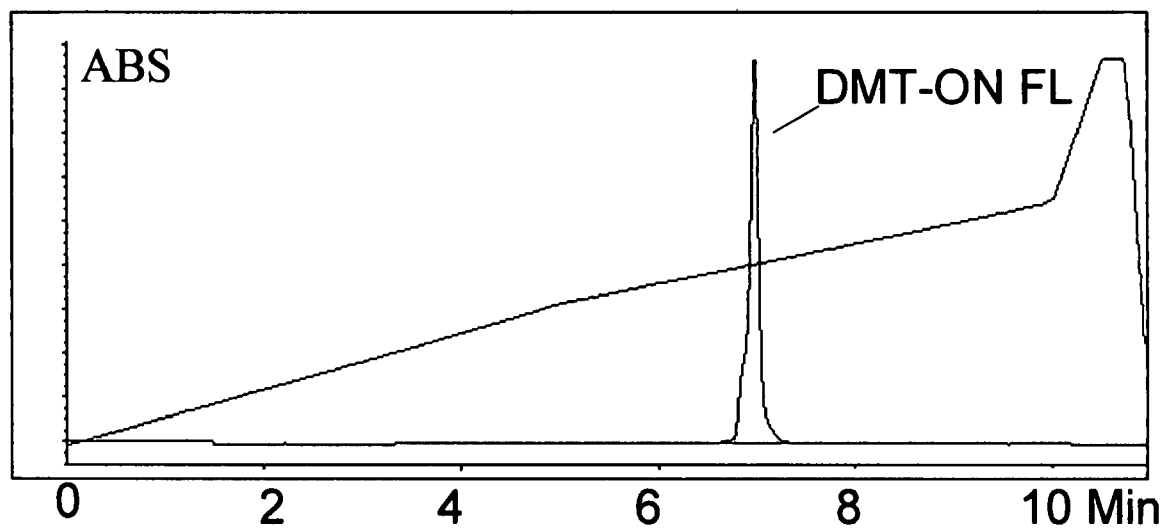

A 70-mers oligonucleotide (with a 51% GC content) was synthesized on a high-throughput synthesizer (BLP 192, Biolytic Lab Performance Inc, Newark Calif.) using a 100 nmol solid support (EZ-frit, Chemistry and Technology for Genes, Milpitas, Calif.) and 5'-DMT protected cyanoethylphosphoramidites. The amidites [dA(Bz), dC(Ac), dG(iBu) or T, 50 mM in acetonitrile] were activated with 5-ethylthiotetrazole (ETT, 250 mM in acetonitrile). The final 5'-DMT groups were not cleaved. Covalently bound oligonucleotides were cleaved from the solid support and deprotected in 28% ammonia (0.5 mL) at 80° C. for 2 hours. RP-HPLC analysis of the crude solution showed around 30% of DMT-off oligonucleotides, 15% of SL DMT-on oligonucleotides, and 55% of FL DMT-on oligonucleotides (see FIG. 3A). The crude solution was purified in 5 minutes using two stacked columns C(1) and C(2), prepacked with tritylmercaptoalkyl-CPG (45-75 μm) embedded in polyethylene (MOP frits, CTGen). Stacked columns C(1)(100/60) and C(2)(100/180) were primed first with 40% acetonitrile in water (1 mL) then TEAA (0.1 M, pH 7.5, 2 mL). The crude solution was diluted with a binding buffer containing 15% NaCl in water and loaded on the stacked columns. The flow-through collected for the purpose of illustration contained very few DMT-on oligonucleotides (see FIG. 3B). Column C(1) was discarded and eluted with 60% acetonitrile in water for the purpose of illustration, yielding the short length DMT-on oligonucleotide fraction (see FIG. 3C). The bottom C(2) column was eluted with 60% acetonitrile yielding purified full length DMT-on 70-mers (see FIG. 3D). The quantities of purified FL DMT-on, flow-through, SL DMT on, and crude oligonucleotides were 15, 20, 2 and 40 ODs, respectively. HPLC analyses were carried out using a Phenomenex Jupiter column (4.60×50 mm, particle size 5 µm) on a HP 1090 instrument. Sample volumes were 20 µL. The column was equilibrated in buffer A (0.1 M TEAA, pH 6.0) and eluted in a gradient of buffer B (H$_2$O/acetonitrile, 1:3, v/v), with a flow rate of 0.5 mL/min.

Example 2

Figure 4A:
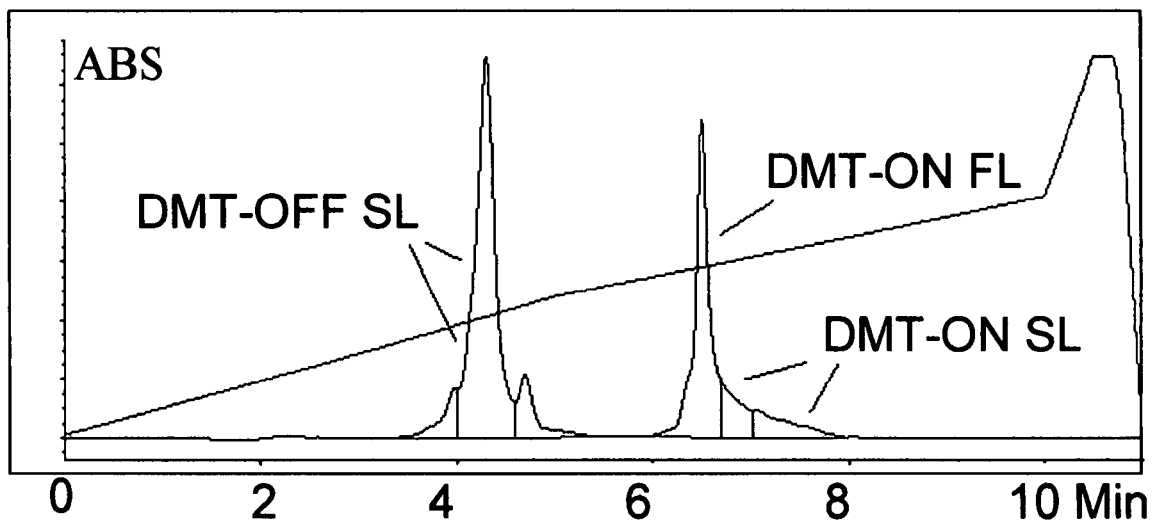
FIGS. 4A to 4E illustrate the purification of a crude DMT-on 125-mers according to method B.
Figure 4B:
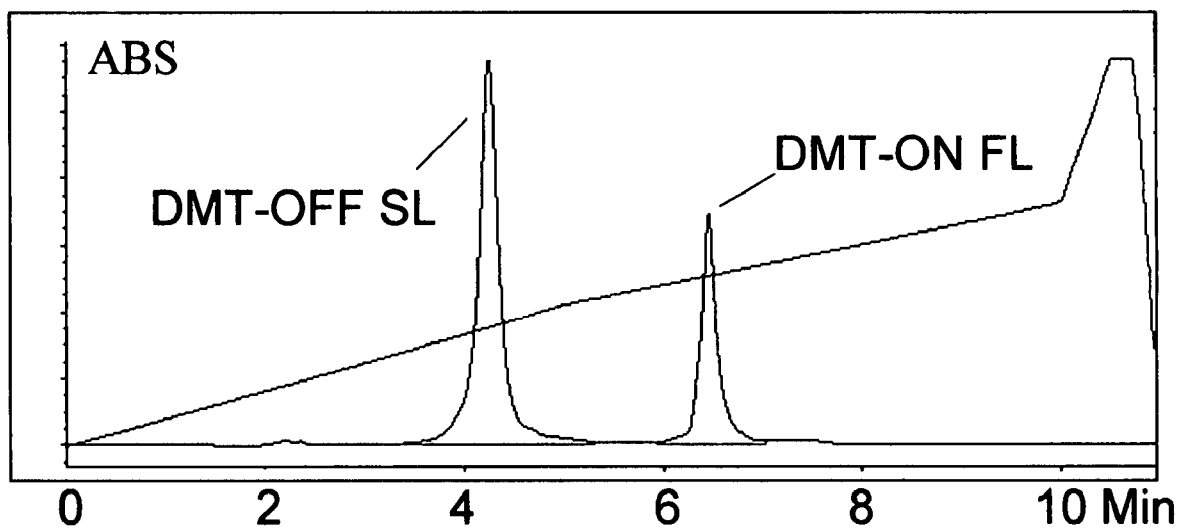
Figure 4C:
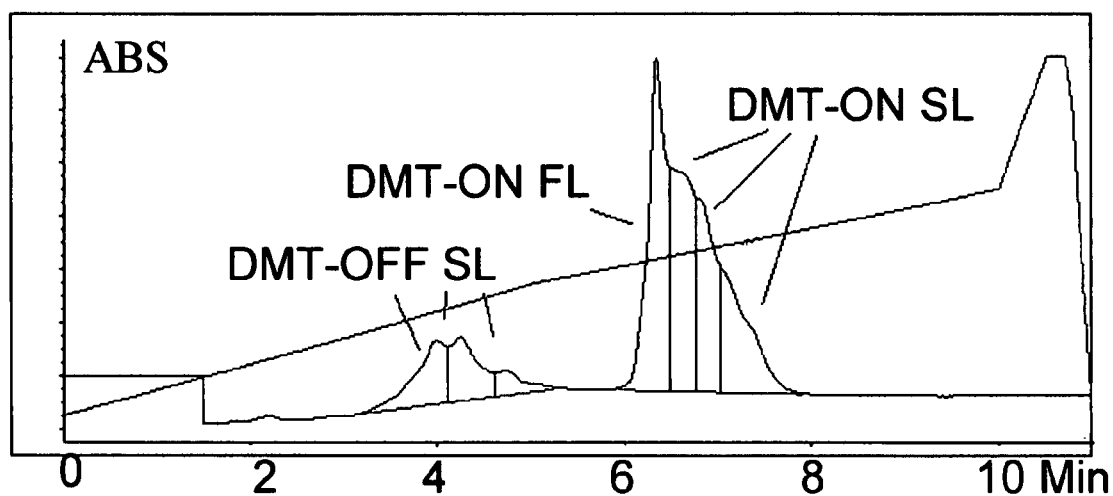
Figure 4D:
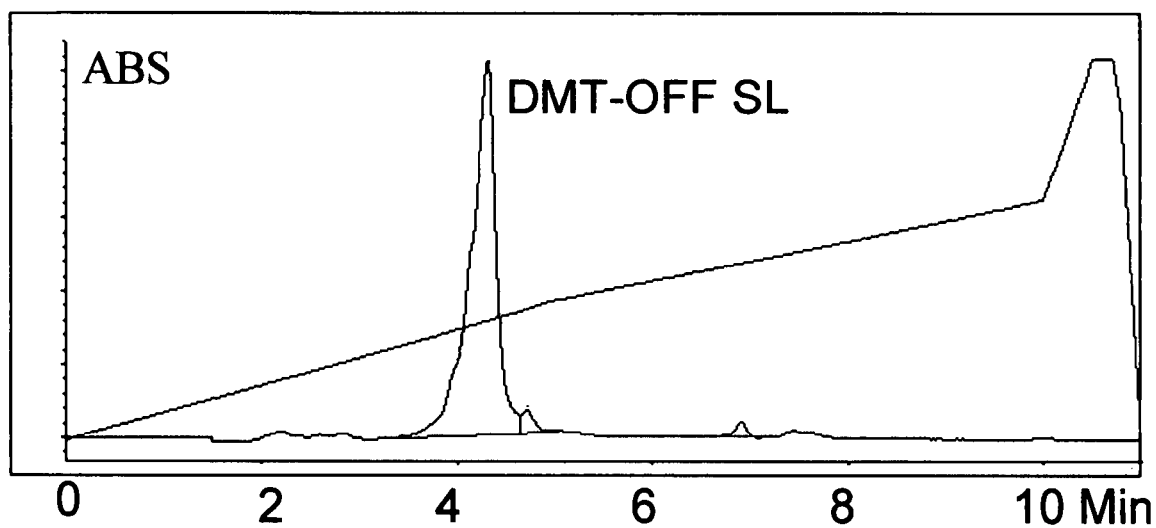
Figure 4E:
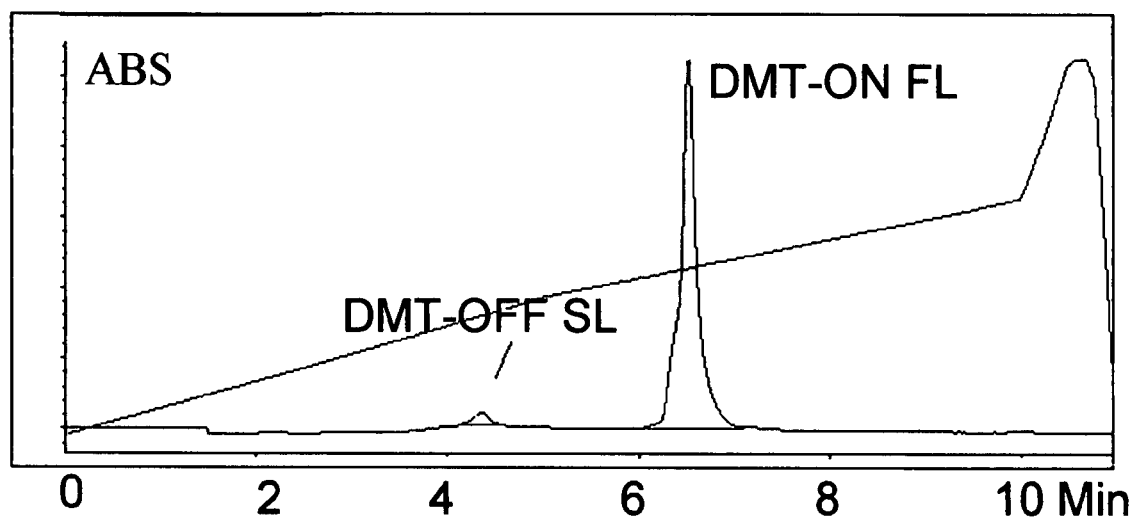

A crude DMT-on 125-mers oligonucleotide (with a 66% GC content) was synthesized on a high-throughput synthesizer (BLP 192, Biolytic Lab Performance Inc) using a 100 nmol synthesis support (EZ-frit, Chemistry and Technology for Genes) and 5'-DMT protected cyanoethylphosphoramidites. The amidites [dA(Bz), dC(Ac), dG(iBu) or T, 50 mM in acetonitrile] were activated with 5-ethylthiotetrazole (ETT, 250 mM in acetonitrile). The final DMT groups were not cleaved. Oligonucleotides bound to the synthesis support were cleaved and deprotected in 28% ammonia (350 µL) at 65° C. for 12 hours. RP-HPLC analysis of the crude solution showed around 40% of DMT-off oligonucleotides, 15% of SL DMT-on oligonucleotides and 45% of FL DMT-on oligonucleotides (see FIG. 4A). The crude solution was diluted with a binding buffer containing 30% NaCl in water (0.8 mL). It was purified in 15 minutes using two stacked columns [C(1)(150/60), C(2)(50/100)] then a third column C(3)(100/300). Columns C(1) to C(2) and C(3) were primed with 40% acetonitrile in water (1 mL) then TEAA (0.1 M, pH 7.5, 2 mL). The crude was loaded on the stacked columns C(1) and C(2) and the flow-through was collected (see FIG. 4B). The said flow-through, containing DMT-off and FL DMT-on oligonucleotides, was reloaded on a third column C(3). The second flow-through was collected for the purpose of illustration and analyzed by RP-HPLC (see FIG. 4D). The FL DMT-on oligonucleotides bound to C(3) were washed with a low salt buffer made of sodium chloride (5%) in water containing few percent of dimethylformamide. Elution of C(3) with 60% acetonitrile yielded purified full length DMT-on 125-mers (see FIG. 4E). The quantity of crude, first flow-through, SL DMT-on, second flow-through and purified FL DMT-on were 50, 40, 10, 30 and 7 ODs, respectively. For the purpose of illustration, stacked columns C(1) to C(2) were eluted with 60% acetonitrile in water to yield the short length DMT-on oligonucleotide fraction (see FIG. 4C). HPLC analyses were carried out using a Phenomenex Jupiter column (4.60×50 mm, particle size 5 µm) on a HP 1090 instrument. Sample volumes were 20 µL. The said column was equilibrated in buffer A (0.1 M TEAA, pH 6.0) and eluted in a gradient of buffer B (H$_2$O/acetonitrile, 1:3, v/v), with a flow rate of 0.5 mL/min.

What we claim is:

1. A method of purifying or separating full length nucleic acids of about 40 bases or more and bearing a 5'-hydrophobic end from a crude solution containing at least two kind of contaminants, the method comprising:
   diluting the solution with a binding buffer and passing the diluted solution through a series of n columns packed with reversed-phase sorbents having differing pore sizes, starting with column(1) and proceeding through column(n), n being a finite integer greater than one; wherein
   one kind of the said contaminants includes truncated nucleic acid without a 5'-hydrophobic end and another kind of the said contaminants includes truncated nucleic acid bearing a 5'-hydrophobic end;
   each of column(1) through column(n−1) has a sorbent with a pore size range selected to preferentially bind a range of sizes of the truncated nucleic acid bearing a 5'-hydrophobic end; and
   column(n) has a sorbent with a pore size range selected to preferentially bind the full length nucleic acid.

2. The method of claim 1, wherein the said truncated nucleic acids bearing a 5'-hydrophobic end preferentially bind to at least one of column(1) through column(n−1) and wherein the said full length nucleic acids preferentially bind to column(n) and the said truncated nucleic acids without a 5'-hydrophobic end are not retained.

3. The method of claim 1, wherein the said truncated nucleic acids bearing a 5'-hydrophobic end preferentially bind to a plurality of stacked columns and wherein a flow-through, containing said full length nucleic acid and said truncated nucleic acids without a 5'-hydrophobic end, is subsequently reloaded on a new column and wherein the said full length nucleic acids consequently bind to the said new column and the said truncated nucleic acids without a 5'-hydrophobic end are not retained, and wherein the plurality of stacked columns and the new column include the series of n columns.

4. The method of claim 1, wherein said full length and truncated nucleic acids bearing a 5'-hydrophobic end bind to said series of columns and said truncated nucleic acids without a 5'-hydrophobic end are not retained.

5. The method of claim 4 further comprising eluting with an eluting solution the said full length and truncated nucleic acids bearing a 5'-hydrophobic end from column(1) through column(n) or just from column(n), adding a binding buffer to the eluting solution, and reloading the resulting mixture on a second series of columns, starting with second series column (1) and proceeding through second series column(m), m being a finite integer greater than one and equaling or differing from n, wherein said truncated nucleic acids bearing a 5'-hydrophobic end preferentially bind to second series column(1) through second series column(m−1) and wherein the said full length nucleic acids preferentially bind to second series column(m).

6. The method of claim 1, wherein said full length nucleic acids are 5'-DMT-on nucleic acids, said truncated nucleic acids with a 5'-hydrophobic end are short length DMT-on nucleic acids and said truncated nucleic acids without a 5'-hydrophobic end are DMT-off nucleic acids; DMT stands for 4,4'-dimethoxytrityl.

7. The method of claim 1 further comprising the step of equilibrating the columns by passing through the reversed-phase sorbents a solution containing acetonitrile in water then a solution containing 0.1M to 1.0 M concentration of monoalkylammonium or dialkylammonium or trialkylammonium acetate at pH ranging from 6 to 9.5.

8. The method of claim 2, further comprising the steps of (a) washing bound full length nucleic acid with a washing buffer which removes contaminants, but not the said bound full length nucleic acid and (b) eluting the bound full length nucleic acid with an eluting buffer.

9. The method of claim 1 wherein the 5'-hydrophobic end is a DMT group and further comprising the steps of (a) washing bound full length nucleic acid with a washing buffer which removes contaminants, (b) on-column detritylating the bound full length nucleic acid with a detritylating solution and (c) eluting the resulting DMT-off nucleic acid with an eluting buffer.

10. The method of claim 9, wherein step (b) further includes washing the detritylated full length nucleic acid with a buffer made of 0.1 M triethylammonium acetate in water.

11. The method of claim 1, wherein the said binding buffer is made of water and sodium chloride, sodium bromide, sodium iodide, potassium chloride, potassium bromide or potassium iodide.

12. The method of claim 1, wherein said full length nucleic acids have length about 40 to 80 bases and the said binding buffer, containing 10 to 20% of sodium chloride, is added in 2:1 to 1:2 volume/volume to the said crude solution.

13. The method of claim 1, wherein said full length nucleic acids have length about 80 to 180 bases and the said binding buffer, containing 15 to 35% of sodium chloride, is added in 1:1 to 1:3 volume/volume to the said crude solution.

14. The method of claim 11, wherein the said binding buffer is further modified with a 2 to 10% concentration of dimethylformamide, dimethylacetamide or dimethylsulfoxide.

15. The method of claim 2, wherein column(1) through column(n−1) are discarded prior to washing truncated nucleic acids without a 5'-hydrophobic end from column(n) with a washing buffer.

16. The method of claim 8, wherein the washing buffer contains a 1 to 5% sodium chloride concentration and a 1 to 10% dimethylformamide concentration sufficient to elute non hydrophobic contaminants but insufficient to elute the full length nucleic acids from the sorbent.

17. The method of claim 9, wherein the said detritylating solution is 2 to 5% dichloroacetic acid or trichloroacetic acid or trifluoroacetic acid in water or 5 to 10% acetic acid in water or combinations thereof.

18. The method of claim 8, wherein the eluting buffer comprises 20 to 60% by volume of an alcohol selected from the group consisting of methanol, ethanol and isopropanol or 25 to 65% by volume of acetonitrile or 15-25% ammonia or 10 to 30% t-butylamine or combinations thereof.

19. The method of claim 1, wherein the said columns consist of cartridges, syringes, or pipette tips that have been prepacked with porous reversed-phase sorbents and are supported in a vacuum tray manifold, wherein the binding buffer and crude solutions are introduced into column(1) and are drawn through by applying a vacuum and wherein a flow-through solution and an elution solution are collected in receiving chambers.

20. The method of claim 1, wherein said sorbents comprise silica particles or controlled pore glass (CPG) beads having an average diameter of about 20 to 45 microns.

21. The method of claim 2, wherein the said series of n columns are packed with porous reversed phase sorbents having well-defined pore size and wherein each of column(1) through column(n−1) has a sorbent with a smaller pore size than the sorbent contained in column(n).

22. The method of claim 2, wherein sorbents contained in each of column(1) through column(n−1) have pores ranging from 40 to 150 Å and wherein sorbent contained in column(n) has pores ranging from 200 to 300 Å.

23. The method of claim 1, wherein the sorbents are made of silica or controlled porous glass having non polar surfaces.

24. The method of claim 23, wherein groups at the said non-polar surfaces are linear or branched alkyl chains selected from C3 to C18.

25. The method of claim 23, wherein groups at the said non-polar surfaces are selected from aryl, benzyl, naphtyl and trityl groups.

26. The method of claim 23, wherein the non-polar surfaces are further endcapped with trialkylsilyl moieties wherein alkyl is selected from methyl, ethyl, propyl, isopropyl, butyl, t-butyl and combinations thereof.

27. The method of claim 1, wherein the columns contain identical sorbents but differing in their pore sizes, or wherein the columns contain sorbents differing in their non polar surface and in their pore sizes.

28. The method according to claim 1 wherein the said nucleic acids are DNA or RNA.

29. The method of claim 12, wherein the said binding buffer is further modified with a 2 to 10% concentration of dimethylformamide, dimethylacetamide or dimethylsulfoxide.

30. The method of claim 13, wherein the said binding buffer is further modified with a 2 to 10% concentration of dimethylformamide, dimethylacetamide or dimethylsulfoxide.

31. The method of claim 9, wherein the washing buffer contains a 1 to 5% sodium chloride concentration and a 1 to 10% dimethylformamide concentration sufficient to elute non hydrophobic contaminants but insufficient to elute the full length nucleic acids from the sorbent.

32. The method of claim 15, wherein the washing buffer contains a 1 to 5% sodium chloride concentration and a 1 to 10% dimethylformamide concentration sufficient to elute non hydrophobic contaminants but insufficient to elute the full length nucleic acids from the sorbent.

33. The method of claim 9, wherein the eluting buffer comprises 20 to 60% by volume of an alcohol selected from the group consisting of methanol, ethanol and isopropanol or 25 to 65% by volume of acetonitrile or 15-25% ammonia or 10 to 30% t-butylamine or combinations thereof.

* * * * *